(12) United States Patent
Choi (10) Patent No.: US 12,378,483 B2
(45) Date of Patent: Aug. 5, 2025

(54) PROCESSES AND SYSTEMS FOR PRODUCING DESULFURIZED ALPHA OLEFINS

(71) Applicant: Saudi Arabian Oil Company, Dhahran (SA)

(72) Inventor: Ki-Hyouk Choi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 131 days.

(21) Appl. No.: 18/149,458

(22) Filed: Jan. 3, 2023

(65) Prior Publication Data

US 2024/0218269 A1 Jul. 4, 2024

(51) Int. Cl.
*C10G 7/08* (2006.01)
*C10G 65/06* (2006.01)
*C10G 65/12* (2006.01)

(52) U.S. Cl.
CPC .............. *C10G 65/12* (2013.01); *C10G 7/08* (2013.01); *C10G 65/06* (2013.01);
(Continued)

(58) Field of Classification Search
CPC .......... C10G 65/12; C10G 7/08; C10G 65/06; C10G 2300/1033; C10G 2300/1088;
(Continued)

(56) References Cited

U.S. PATENT DOCUMENTS 4,946,560 A * 8/1990 Slaugh ................. C07C 5/25
203/91
11,046,624 B1 6/2021 Choi et al.
(Continued)

OTHER PUBLICATIONS

Notification of Transmittal of the International Search Report and the Written Opinion of the International Searching Authority, or the Declaration dated Mar. 18, 2024 pertaining to International application No. PCT/US2023/081822 filed Nov. 30, 2023, pp. 1-14.

*Primary Examiner* — Prem C Singh
*Assistant Examiner* — Francis C Campanell
(74) *Attorney, Agent, or Firm* — DINSMORE & SHOHL LLP (57) ABSTRACT

A process for producing desulfurized alpha olefins may include reacting a conjugated diene compound and a hydrocarbon oil stream including alpha olefins in a Diels-Alder reactor at a temperature of 100° C. to 250° C. to form an effluent stream including adducts of the conjugated diene compound and the alpha olefins, subjecting the effluent stream to a hydrodesulfurization catalyst and a hydrogen stream in a hydrodesulfurization reactor to produce a hydrodesulfurized effluent stream including the adducts, a saturated $C_{5+}$ hydrocarbon stream, and a gaseous stream, separating the adducts, the saturated $C_{5+}$ hydrocarbon stream, and the gaseous stream, and cracking the adducts in a first thermal cracking reactor operating at a temperature greater than 250° C. to produce a decomposed adducts stream including an alpha olefin stream and a recovered conjugated diene compound stream, wherein the gaseous stream includes hydrogen, sulfides, $C_1$-$C_4$ saturated hydrocarbons, or combinations thereof.

20 Claims, 2 Drawing Sheets

(52) U.S. Cl.
CPC ............... *C10G 2300/1033* (2013.01); *C10G 2300/1088* (2013.01); *C10G 2300/202* (2013.01); *C10G 2300/4006* (2013.01)

(58) Field of Classification Search
CPC ...... C10G 2300/202; C10G 2300/4006; C10G 9/00; C10G 29/205; C10G 45/10; C10G 69/06; C10G 45/08; C07C 2603/88; C07C 2/50
USPC .......................................................... 585/257
See application file for complete search history.

(56) References Cited

U.S. PATENT DOCUMENTS

| | | |
|---|---|---|
| 2002/0165420 A1 | 11/2002 | Elomari et al. |
| 2012/0061294 A1 | 3/2012 | Choi et al. |
| 2020/0291305 A1 | 9/2020 | Mukherjee et al. |
| 2022/0213395 A1* | 7/2022 | Koseoglu ................ C10G 9/36 |

* cited by examiner

PROCESSES AND SYSTEMS FOR PRODUCING DESULFURIZED ALPHA OLEFINS

TECHNICAL FIELD

Embodiments of the present disclosure generally relate to processes and systems for refining and upgrading hydrocarbon oil, and pertain particularly to processes and systems for producing desulfurized alpha olefins.

BACKGROUND

Olefins and aromatic compounds, such as ethylene, propylene, butylene, butadiene, benzene, toluene, and xylenes, are basic intermediates for many petrochemical industries. Alpha olefins are a particularly desired subset of the olefin species wherein the carbon double bond occurs in the terminal (or alpha) position.

Olefins are usually obtained through the thermal cracking (or steam pyrolysis) of petroleum gases and distillates such as ethane, propane, butane, naphtha, kerosene, or gas oil. These compounds are also produced through refinery fluidized catalytic cracking (FCC) process where standard heavy feedstocks, such as gas oils or residues, are converted. Typical FCC feedstocks range from hydrocracked bottoms to heavy feed fractions, such as vacuum gas oil and atmospheric residue. However, these feedstocks are limited.

SUMMARY

Accordingly, despite the options available for producing a greater yield of propylene and other olefins, such as alpha olefins, intense research activity in this field is still being conducted. Particularly, to address the limited feedstocks for traditional olefin generation, methods of producing light olefins from a crude oil source are still being investigated. However, crude oil sources can be considered 'sour', meaning that the feedstock contains a high amount of impurities (including sulfur, nitrogen, and coke, a high carbon petroleum residue), as opposed to 'sweet', containing a trace amount of impurities. These impurities can cause a variety of harmful effects if present in non-trace amounts in upgraded feeds, such as poisoning catalysts used in later upgrading, as well as potentially lowering the economic value of the upgraded feed.

Further complicating matters, traditional methods of removing the contaminants, such as in hydrodesulfurization processes, may saturate olefins present in the stream, making the contaminant removal costly to the desired yield of olefins. Further yet, the preferential saturation of these olefins in the hydrogenation process may reduce the efficiency of the desulfurization as a whole.

Consequently, new processes are desired that produce alpha olefins with a low contaminant content, i.e. are sweet, but also do not negatively impact alpha olefin yield of the process. Described herein are systems and processes for producing desulfurized alpha olefins, while providing the aforementioned benefits.

Particularly as explained in more detail herein, the reaction of a conjugated diene compound with alpha olefin components of a hydrocarbon oil stream may produce an effluent stream of adducts of the conjugated diene compound and the alpha olefin. When the effluent stream is later desulfurized in a hydrodesulfurization reactor, the adducts do not participate in the reaction, resulting in less loss of yield to saturation and greater removal of contaminant (sulfur) fractions. The saturated non-adduct fractions and contaminants may then be more easily separated from the adduct stream due to the differences in boiling point from the hydrodesulfurization reactions. The alpha olefins may then be recovered from the adducts in a desulfurized form by a decomposition reaction, resulting in a desulfurized alpha olefin product and recovered conjugated diene compounds that may be reused.

In accordance with one embodiment herein, a process for producing desulfurized alpha olefins may include reacting a conjugated diene compound and a hydrocarbon oil stream including alpha olefins in a Diels-Alder reactor at a temperature of 100° C. to 250° C. to form an effluent stream including adducts of the conjugated diene compound and the alpha olefins. The process may further include subjecting the effluent stream to a hydrodesulfurization catalyst and a hydrogen stream in a hydrodesulfurization reactor to produce a hydrodesulfurized effluent stream including the adducts, a saturated $C_{5+}$ hydrocarbon stream, and a gaseous stream. The process may further yet include separating the adducts, the saturated $C_{5+}$ hydrocarbon stream, and the gaseous stream, wherein the gaseous stream includes hydrogen, sulfides, $C_1$-$C_4$ saturated hydrocarbons, or combinations thereof. The process may further yet include cracking the adducts in a first thermal cracking reactor operating at a temperature greater than 250° C. to produce a decomposed adducts stream including an alpha olefin stream and a recovered conjugated diene compound stream.

According to another embodiment herein, a system for producing desulfurized alpha olefins may include a Diels-Alder reactor, a hydrodesulfurization reactor fluidly connected to and downstream of the Diels Alder reactor, a first distillation tower fluidly connected to and downstream of the hydrodesulfurization reactor, a first thermal cracking reactor fluidly connected to and downstream of the first distillation tower, and a second distillation tower fluidly connected to and downstream of the first thermal cracking reactor. The Diels-Alder reactor may be configured to form an effluent stream from a hydrocarbon oil stream and a conjugated diene compound, the effluent stream comprising adducts of the conjugated diene compound and alpha olefins from the hydrocarbon oil stream. The hydrodesulfurization reactor may include a hydrodesulfurization catalyst.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which.

Figure (FIG.) 1 illustrates a process flow diagram for an exemplary process in accordance with embodiments described herein.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in reactors, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines, which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows, which do not connect two or more system components, signify a product stream, which exits the depicted system, or a system inlet stream, which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in embodiments, less than all of the stream signified by an arrow may be transported between the system components, such as if a slip stream is present.

It should be understood that two or more process streams are "mixed" or "combined" when two or more lines intersect in the schematic flow diagrams of the relevant figures. Mixing or combining may also include mixing by directly introducing both streams into a like reactor, separation unit, or other system component. For example, it should be understood that when two streams are depicted as being combined directly prior to entering a separation unit or reactor, that in embodiments the streams could equivalently be introduced into the separation unit or reactor and be mixed in the reactor. Alternatively, when two streams are depicted to independently enter a system component, they may in embodiments be mixed together before entering that system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to processes and systems for producing desulfurized alpha olefins, while providing the aforementioned benefits.

As used herein, "alpha olefins" refers to an olefin wherein the carbon double bond occurs in the terminal (or alpha) position. For example, alpha olefins may have the general formula:

$$CH_2 = CH - R_1$$

wherein $R_1$ is an alkyl hydrocarbon group containing from 1 to 30 hydrocarbon atoms. "Linear alpha olefins" refer to a sub-category of alpha olefins that is distinguishable from "branched alpha olefins" by the linearity of the of hydrocarbon chain versus the non-linearity for the branched alpha olefins. "Internal olefins," as used herein, refer to olefins wherein the carbon double bond occurs in the second (beta) position or greater, such as the gamma position, delta position, epsilon position, and so on. For example, internal olefins may have the general formula:

$$R_1 - CH = CH - R_2$$

wherein $R_1$ and $R_2$ may be the same or different and are each an alkyl hydrocarbon group containing from 1 to 15 hydrocarbon atoms. As used herein, "internal olefins" may also be referred to as "non-alpha olefins" referring to the carbon double bond not being in the alpha position.

As used herein, a "catalyst" refers to any substance that increases the rate of a specific chemical reaction. Catalysts described in this disclosure may be utilized to promote various reactions, such as, but not limited to, cracking (including aromatic cracking), isomerization, demetalization, desulfurization, and denitrogenation. As used herein, "cracking" generally refers to a chemical reaction where carbon-carbon bonds are broken. For example, a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

As used herein, the term "crude oil" is to be understood to mean a mixture of petroleum liquids, gases, or combinations of liquids and gases, including some impurities such as sulfur-containing compounds, nitrogen-containing compounds and metal compounds that have not undergone significant separation or reaction processes. Crude oils are distinguished from fractions of crude oil. As used herein, the crude oil may be a minimally treated crude oil to provide a hydrocarbon oil feedstock having total metals (Nickel+Vanadium) content of less than 5 parts per million by weight (ppmw) and Conradson carbon residue of less than 5 wt. % Such minimally treated materials may be considered crude oils as described herein.

As used herein, "desulfurized" may refer to a substance having a sulfur content of less than 20 parts per million.

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used herein, the term "naphtha" refers to a mixture of substances primarily including $C_5$ to $C_{12}$ hydrocarbons. "Light naphtha," as used herein, is a fraction of naphtha primarily including $C_5$ to $C_6$ hydrocarbons. As used herein, the term "heavy naphtha" refers to a fraction of naphtha primarily including $C_7$ to $C_{12}$ hydrocarbons.

As used herein, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Exemplary reactors include packed bed reactors such as fixed-bed reactors, and fluidized bed reactors. One or more "reaction zones" may be disposed in a reactor. As used herein, a "reaction zone" refers to an area where a particular reaction takes place in a reactor. For example, a packed bed reactor with multiple catalyst beds may have multiple reaction zones, where each reaction zone is defined by the area of each catalyst bed.

As used herein, "residence time," refers to the amount of time taken for a feed stream to enter and then exit the treatment units, reactors, and separators discussed herein.

As used herein, a "separation unit" or "separator" refers to any separation device that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, distillation towers, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used herein, one or more chemical constituents may be "separated" from a process stream to form a new process stream. Generally, a process stream may enter a separation unit and be divided, or separated, into two or more process streams of desired composition. Further, in some separation processes, a "lower boiling point fraction" (sometimes referred to as a "light fraction" or "light fraction stream") and a "higher boiling point fraction" (sometimes referred to as a "heavy fraction," "heavy hydrocarbon fraction," or "heavy hydrocarbon fraction stream") may exit the separation unit, where, on average, the contents of the lower boiling point fraction stream have a lower boiling point than the higher boiling point fraction stream. Other streams may fall between the lower boiling point fraction and the higher boiling point fraction, such as a "medium boiling point fraction."

It should further be understood that streams may be named for the components of the stream, and the component for which the stream is named may be the major component of the stream (such as including from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. By way of non-limiting example, a referenced "$C_1$-$C_4$ hydrocarbon stream" passing from a first system component to a second system component should be understood to equivalently disclose "$C_1$-$C_4$ hydrocarbons" passing from a first system component to a second system component, and the like.

Figure 1:
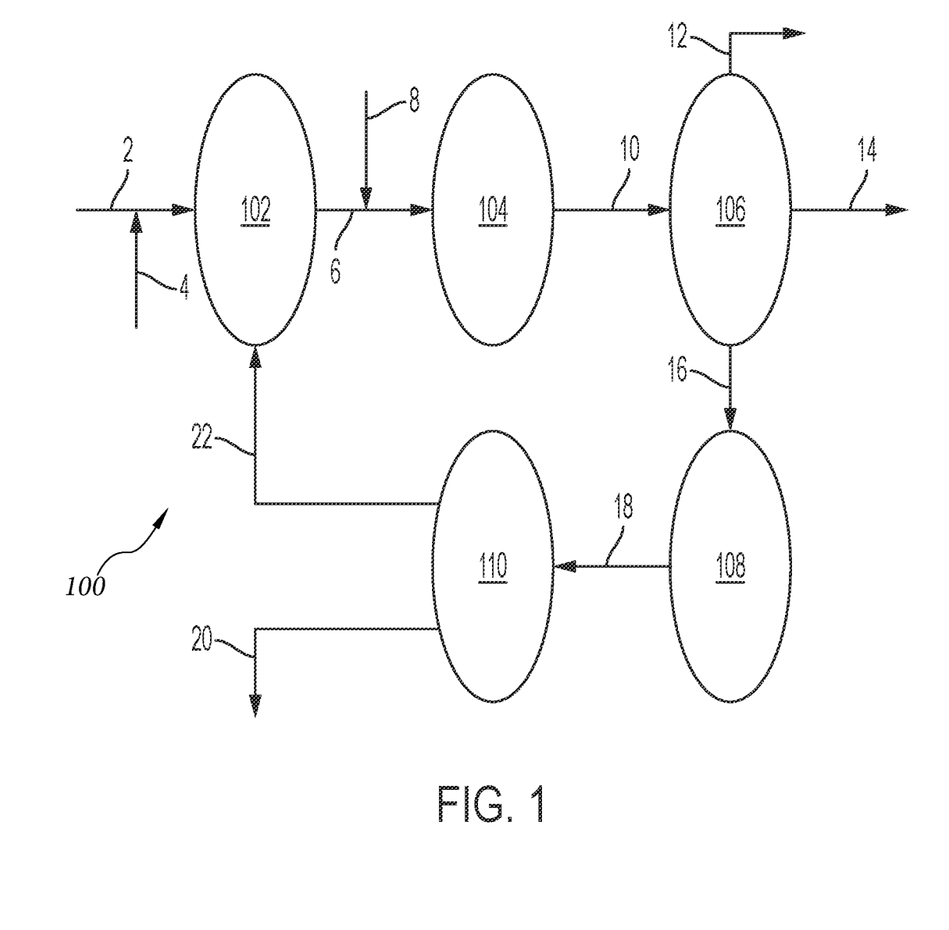

Referring initially to FIG. 1, a system 100 for producing desulfurized alpha olefins from a hydrocarbon oil feedstock 2 is illustrated. As used herein, "feed stock" may also be used to refer to "feed stream(s)." The system 100 includes a Diels-Alder reactor 102, a hydrodesulfurization reactor 104, a separator 106, a thermal cracking reactor 108, and a second distillation tower 110.

Still referring to FIG. 1, and in embodiments, hydrocarbon oil stream 2 may include crude oils including but not limited to: whole crude oil, distilled crude oil, residue oil, topped crude oil, liquefied coals, and hydrocarbons produced from plastic decomposition. The distilled crude oil may include crude oil fractions including but not limited to paraffin and naphtha. As described herein, "topped crude oil" is understood to mean a fraction of crude oil with boiling points higher than 160° C. The hydrocarbon oil stream 2 may also include the previous crude oils that have been additionally subjected to one or more upgrading processes, including but not limited to thermal cracking, steam cracking, catalytic cracking, or combinations thereof, i.e., the hydrocarbon oil stream may include an upgraded crude oil.

Figure 2:
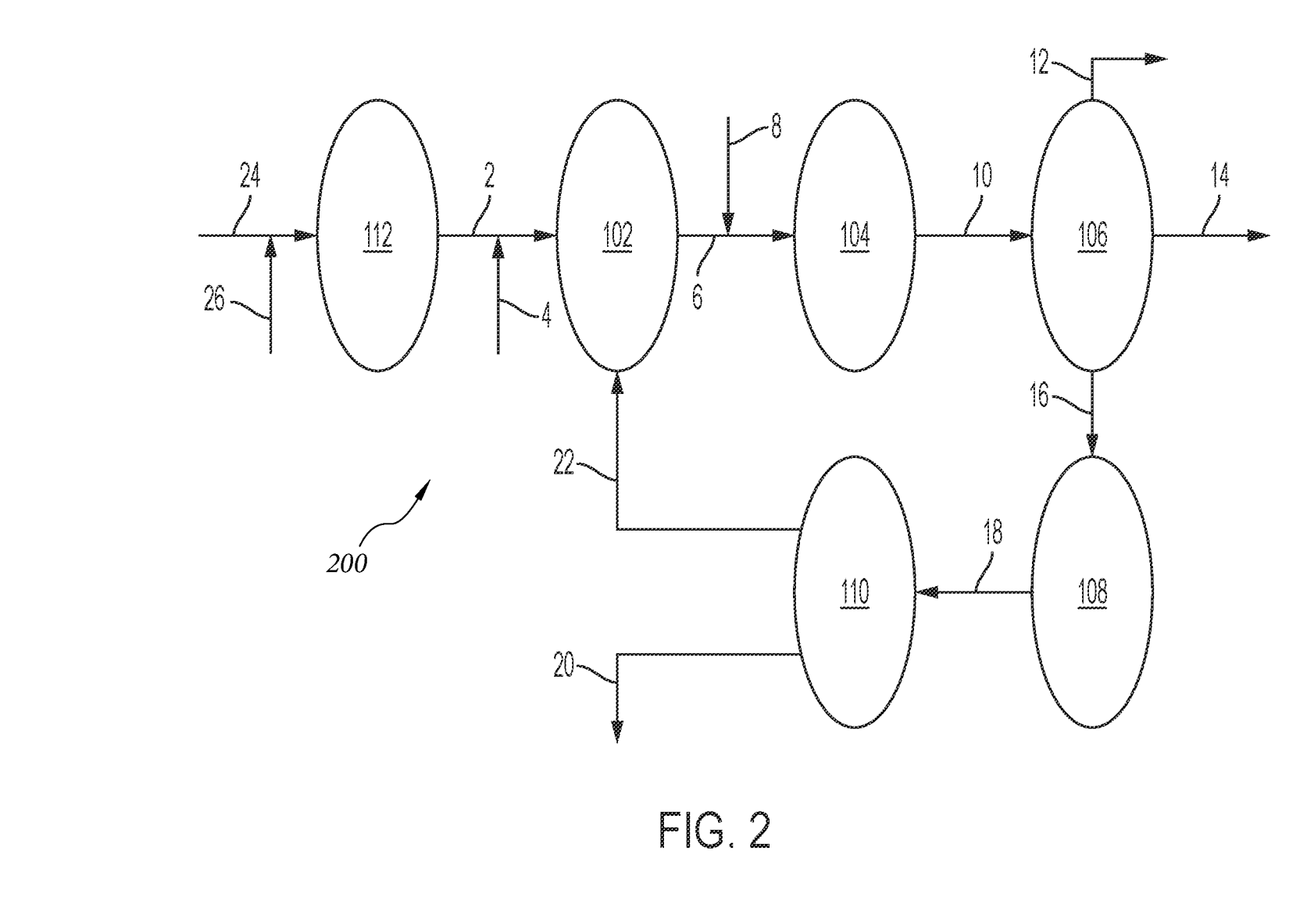
FIG. 2 illustrates another process flow diagram for an exemplary process in accordance with embodiments described herein.

While the present description and examples may specify hydrocarbon oil 2 as the feedstock stream, it should be understood that the systems 100 and 200, described with respect to the embodiment of FIGS. 1 and 2, may be applicable for the conversion of a wide variety of crude oils, which may be present in the hydrocarbon oil stream 2. The hydrocarbon oil stream 2 may include one or more non-hydrocarbon constituents, such as one or more heavy metals, sulfur compounds, nitrogen compounds, inorganic components, or other non-hydrocarbon compounds. The hydrocarbon oil stream 2 may have a sulfur content of greater than 20 ppm, such as from 20 ppm to 100 ppm, from 100 ppm to 500 ppm, from 500 ppm to 1000 ppm, from 1000 ppm to 2000 ppm, from 2000 ppm to 10,000 ppm, from 10,000 ppm to 25,000 ppm, from 25,000 to 50,000 ppm, or any combination of ranges or smaller range therein, such as from 20 ppm to 50,000 ppm. In other words, the hydrocarbon oil stream 2 may, in at least some embodiments, be considered 'sour.' The sulfur compounds may include but may not be limited to sulfides, thiols, disulfides, thiophenes, aryl sulfides, benzothiophenes, dibenzothiophenes, or combinations thereof.

In embodiments, hydrocarbon oil stream 2 may be a heavy crude oil, which includes crude oil having an American Petroleum Institute (API) gravity of less than 35°, 34.5°, 34°, or 33°. By way of non-limiting example, the hydrocarbon oil stream 2 may be Arab Heavy crude oil, which has an API gravity of approximately 28°. In embodiments, the hydrocarbon oil stream 2 may be a light crude oil, which includes crude oil having an American Petroleum Institute (API) gravity of greater than 35°, 36°, 37°, or 38°. By way of non-limiting example, the hydrocarbon oil stream 2 may be Arab Light crude oil, which has an API gravity of approximately 33°. In embodiments, the hydrocarbon oil stream 2 may be an extra light crude oil, which includes crude oil having an American Petroleum Institute (API) gravity of greater than 39°, 40°, 41°, or 42°. By way of another non-limiting example, the hydrocarbon oil stream 2 may be Arab Extra Light crude oil, which has an API gravity of approximately 39°. In embodiments, the hydrocarbon oil stream 2 may be a combination of heavy, light, and extra light crude oils, and may include crude oils with an API gravity of from 25° to 50°.

Still referring to FIG. 1, the Diels-Alder reactor 102 may form an effluent stream 6 from a hydrocarbon oil stream 2 and a conjugated diene compound 4. The effluent stream 6 may include adducts of the conjugated diene compound and alpha olefins that may be included in the hydrocarbon oil stream 2. The hydrocarbon oil stream may also include non-alpha olefins (internal olefins), as previously described. As used herein, the term "Diels-Alder" refers to a category of chemical reactions involving a cycloaddition reaction between a conjugated diene and a substituted alkene, which is commonly referred to as a dienophile. The products of the reaction are adducts generally in the form of a substituted cyclohexene derivative. For example, and in embodiments herein, an alpha olefin and conjugated diene (for example, anthracene) may be reacted to break the carbon double bond of the alkene and two double bonds of the conjugated diene. Thereby, the alkene and the conjugated diene compound form a saturated bridged ring, as shown in the example illustration below. Without being limited by theory, the saturated bridged ring may be more stable than an unsaturated carbon—carbon bond, and may thus be less susceptible to attack in a hydrodesulfurization reaction. In other words, the saturated bridge ring may be inert in hydrodesulfurization reactions.

Equation 1: Exemplary Diels-Alder Reaction

FIG. 1

As previously discussed, the effluent stream 6 may include adducts of the conjugated diene compound 4 and alpha olefins. The alpha olefins may include linear alpha olefins or branched linear olefins. However, without being limited by theory, the adducts of the conjugated diene compound 4 and the alpha olefins may include primarily (greater than or equal to 50 wt. %) adducts of the linear alpha olefins rather than the branched alpha olefins. This may be due to the steric hindrance exerted by the branch(es) of the branched alpha olefins vs. the non-branched linear alpha olefins. Particularly, the steric hindrance may limit the reaction rate of branched alpha olefins in the Diels-Alder reaction.

In embodiments, a molar ratio of the conjugated diene compound 4 to the alpha olefins in the hydrocarbon oil stream 2 may be from 0.1:1 to 5:1, from 0.1:1 to 1:1, from 1:1 to 3:1, from 3:1 to 5:1 moles of conjugated diene compound to moles alpha olefin, or any combination of ranges or smaller range therein.

In embodiments, the effluent stream 6 may also include adducts of the conjugated diene compound 4 and the internal olefins. However without being limited by theory, and similar to the adducts of the conjugated diene compound 4 and the branched alpha olefins, steric hindrance exerted from the one or more alkyl groups surrounding the carbon-carbon double bond of the internal olefins may limit the reaction rate of internal olefins that participate in the Diels-Alder reactions. This steric hindrance may result in the effluent stream 6 comprising primarily alpha olefin adducts over internal olefin adducts.

In the embodiments herein, various reactors are considered suitable for the Diels-Alder reactor 102. For example, and in embodiments, the Diels-Alder reactor 102 may be a tubular-type reactor, vessel-type reactor, or continuous stirred-tank reactor (CSTR) or batch-type reactor such as an autoclave reactor. In other words, the Diels-Alder 102 reactor may be configured to form the effluent stream 6 in batch mixing or continuous mixing. In embodiments, the Diels-Alder reactor 102 may be operated at a temperature of from 100° C. to 250° C., from 100° C. to 225° C., from 100° C. to 200° C., from 100° C. to 150° C., from 100° C. to 125° C., from 125° C. to 250° C., from 125° C. to 225° C., from 125° C. to 200° C., from 125° C. to 150° C., from 150° C. to 250° C., from 150° C. to 225° C., from 150° C. to 200° C., from 200° C. to 250° C., from 200° C. to 225° C., from 225° C. to 250° C., or any combination of ranges or any smaller range therein, such as from 240° C. to 245° C.

The Diels-Alder reactor 102 may also be operated at a pressure of from 0.20 Megapascals (MPa) to 3.55 MPa, such as from 0.20 MPa to 0.45 MPa, from 0.45 MPa to 0.79 MPa, from 0.79 MPa to 1.83 MPa, from 1.83 MPa to 2.86 MPa, from 2.86 MPa to 3.55 MPa, or any combination of ranges or smaller range therein. The Diels-Alder reactor 102 may also operate with a residence time of between 0.1 hours to 10 hours. The Diels-Alder reactor 102 may operate with a residence time of from 0.1 hours to 1 hour, from 1 hour to 2 hours, from 2 hours to 5 hours, from 5 hours to 8 hours, from 8 hours to 10 hours, or any combination of ranges or smaller range therein, such as from 2 hours to 8 hours.

The conjugated diene compound 4 may include a polycyclic aromatic hydrocarbon having at least 2 double bonds. As used herein, "polycyclic" means a composition having multiple rings. These rings may be fused, bridged, unfused. Moreover, these polycyclic compounds may include one or more aromatic compositions. In one or more embodiments, the conjugated diene compound 4 may include substituted anthracene, unsubstituted anthracene, cyclohexadiene, cyclopentadiene, or combinations thereof.

As previously described, the reaction of the conjugated diene compound 4 and the hydrocarbon oil stream 2 may form adducts of the conjugated diene compound 4 and at least alpha olefins within the hydrocarbon oil stream 2, as in a Diels-Alder reaction. Without being limited by theory and in embodiments, at least some of the sulfur compounds within the hydrocarbon oil stream 2 may be inert in the Diels-Alder reaction, especially at pressures of less than approximately 5.62 MPa. The inert sulfur compounds may include, but may not be limited to thiols, sulfide, disulfide, thiophenes, benzothiophenes, dibenzothiophenes, or combinations thereof. Thereby, the Dies-Alder reactions described herein may exclude the inert sulfur compounds, allowing the same to be easily separated in hydrodesulfurization reactions.

Still referring to FIG. 1, the hydrodesulfurization reactor 104 may be fluidly connected to, and downstream from, the Diels-Alder reactor 102. As used herein, the hydrodesulfurization reactor 104 may also be regarded as a hydrotreater. The hydrodesulfurization reactor 104 may include a hydrodesulfurization catalyst. The hydrodesulfurization reactor 104 may desulfurize the effluent stream 6 in the presence of a hydrogen stream 8 to produce a hydrodesulfurized effluent 10. The hydrodesulfurized effluent 10 may include a gaseous stream 12, a saturated $C_{5+}$ hydrocarbon stream 14, and the adducts 16 of the conjugated diene compound 4 and the alpha olefins. The saturated $C_{5+}$ hydrocarbon stream 14 and the adducts 16 may together comprise a liquid stream. The gaseous stream may include hydrogen, sulfides (such as hydrogen sulfide), $C_1$-$C_4$ saturated hydrocarbons, or combinations thereof.

Without being limited by theory, the hydrodesulfurization reactions within the hydrodesulfurization reactor 104 may operate to decompose and saturate the sulfur compounds present within the effluent stream 6, and particularly the non-adduct portion of the effluent stream 6, with the hydrogen stream 8, thereby converting sulfur compounds to hydrogen sulfide. The sulfides may then be more easily removed from the hydrodesulfurized effluent 10 as part of the gaseous stream 12. In other words, the adducts of the conjugated diene compound 4 and at least the alpha olefins may be inert in the hydrodesulfurization reactions.

As used herein, a "saturated hydrocarbon" refers to a hydrocarbon chain that contain only single bonds between carbon atoms. In like manner, a hydrocarbon becoming saturated may refer to a hydrogenation reaction wherein carbon-carbon double or triple bonds are converted into carbon-carbon single bonds, and thereby an alkene (olefin) or alkyne may be converted into an alkane (paraffin) during hydrogenation.

As previously stated, the hydrodesulfurization reactor 104 may include a hydrodesulfurization catalyst. The hydrodesulfurization catalyst may include an active-phase metal on a support. The active-phase metal may include a first metal and a second metal. The first and/or second metals may be selected from the group consisting of iron, ruthenium, osmium, cobalt, rhenium, iridium, nickel, palladium, tungsten, molybdenum, and platinum. The support may be selected from activated carbon, activated carbon fiber, carbon black, activated carbon fabric, activated carbon honeycomb, silicon dioxide, titanium dioxide, aluminum oxide, and zirconium dioxide. Accordingly, the hydrodesulfurization catalyst may be selected from CoMo on aluminum oxide, silica oxide, or activated carbon; NiMo on aluminum oxide, silica oxide, or activated carbon; and NiCoMo on aluminum oxide, silica oxide, and activated carbon.

The hydrodesulfurization catalyst may include from 2 wt. % to 50 wt. % molybdenum measured by weight of the hydrodesulfurization catalyst, such as from 2 wt. % to 5 wt. % from 5 wt. % to 10 wt. %, from 10 wt. % to 20 wt. %, from 20 wt. % to 25 wt. %, from 25 wt. % to 30 wt. %, from 30 wt. % to 50 wt. %, or any combination of ranges, or smaller range therein, such as from 2 wt. % to 10 wt. % molybdenum by weight of the hydrodesulfurization catalyst.

The hydrodesulfurization catalyst may include from 0.2 wt. % to 20 wt. % cobalt measured by weight of the hydrodesulfurization catalyst, such as from 0.2 wt. % to 0.5 wt. %, from 0.5 wt. % to 1 wt. %, from 1 wt. % to 2 wt. %, from 2 wt. % to 5 wt. %, from 5 wt. % to 10 wt. %, from 10 wt. % to 15 wt. %, from 15 wt. % to 20 wt. %, or any combination of ranges, or smaller range therein, such as from 2 wt. % to 10 wt. % cobalt by weight of the hydrodesulfurization catalyst.

The hydrodesulfurization catalyst may include from 0.2 wt. % to 20 wt. % nickel measured by weight of the hydrodesulfurization catalyst, such as from 0.2 wt. % to 0.5 wt. %, from 0.5 wt. % to 1 wt. %, from 1 wt. % to 2 wt. %, from 2 wt. % to 5 wt. %, from 5 wt. % to 10 wt. %, from 10 wt. % to 15 wt. %, from 15 wt. % to 20 wt. %, or any combination of ranges, or smaller range therein, such as from 2 wt. % to 10 wt. % nickel by weight of the hydrodesulfurization catalyst.

In the embodiments herein, various reactors are considered suitable for the hydrodesulfurization reactor 104. For example, and in embodiments, the hydrodesulfurization reactor 104 may be a tubular-type reactor, vessel-type reactor, batch type reactor such as autoclave reactor, or continuous stirred-tank reactor (CSTR). In other words, the hydrodesulfurization reactor 104 may be configured to form the hydrodesulfurized effluent 10 in batch mixing or continuous mixing. In embodiments, the hydrodesulfurization reactor 104 may be operated at a temperature of from 100° C. to 350° C., from 100° C. to 225° C., from 100° C. to 200° C., from 100° C. to 150° C., from 100° C. to 125° C., from 125° C. to 250° C., from 125° C. to 225° C., from 125° C. to 200° C., from 125° C. to 150° C., from 150° C. to 250° C., from 150° C. to 225° C., from 150° C. to 200° C., from 200° C. to 250° C., from 200° C. to 225° C., from 225° C. to 250° C., or any combination of ranges or any smaller range therein, such as from 100° C. to 250° C. The hydrodesulfurization reactor 104 may also be operated at a pressure of from 0.58 MPa to 4.24 MPa, such as from 0.58 MPa to 0.79 MPa, from 0.79 MPa to 1.48 MPa, from 1.48 MPa to 2.86 MPa, from 2.86 MPa to 3.55 MPa, from 3.55 MPa to 4.24 MPa, or any combination of ranges or smaller range therein.

In embodiments, the hydrodesulfurization reactor 104 may operate with a residence time of between 6 minutes to 60 minutes. The hydrodesulfurization reactor 104 may operate with a residence time of from 6 minutes to 15 minutes, from 15 minutes to 20 minutes, from 20 minutes to 40 minutes, from 40 minutes to 50 minutes, from 50 minutes to 55 minutes, from 55 minutes to 60 minutes, or any combination of ranges or smaller range therein.

The hydrodesulfurization reactor 104 may also have a hydrogen stream 8 injection rate of from 100 m³ hydrogen per m³ of effluent stream to 1000 m³ hydrogen per m³ of effluent stream, preferably from 200 m³ hydrogen per m³ effluent stream to 400 m³ hydrogen per m³ of effluent stream at normal conditions (0° C. and 1 atmosphere).

In embodiments, the hydrodesulfurization reactor 104 may further include a high pressure separator on the downstream end of the hydrodesulfurization reactor 104. The high pressure separation unit may be fluidly connected to the hydrodesulfurization unit 104 and may be operable to separate the liquid stream (the adducts 16 and the saturated $C_{5+}$ hydrocarbon stream 14) from the gaseous stream 12. The high pressure separation unit may operate at a pressure of approximately the same as the hydrodesulfurization reactor 104. In other words, the operating pressure of the hydrodesulfurization reactor 104 may not be let off before entry into the high pressure separator. In embodiments, the high pressure separator may include an operating and outlet pressure of from 1 MPa to 4.24 MPa.

The hydrodesulfurization reactor may also further include a low pressure separator on downstream end of the high pressure separator. The low pressure separator may operate at a relatively lower pressure than the high pressure separator, and may in some embodiments be operable to reduce the pressure of the gaseous stream 12 and the liquid stream to approximately atmospheric pressure. In embodiments, the low pressure separator may also be operable to lower the pressure of the gaseous stream 12 and the liquid stream to a pressure of from 0 MPa to 4.24 MPa.

Still referring to FIG. 1, the system 100 may further include the separator 106. The separator 106 may be fluidly connected to, and downstream of, the hydrodesulfurization reactor 104. The separator 106 may operate to separate the adducts 16, the saturated $C_{5+}$ hydrocarbon stream 14, and the gaseous stream 12.

In embodiments, the separator 106 may be regarded as a first distillation tower 106. The first separator 106 may be fluidly connected to, and downstream of, the hydrodesulfurization reactor 104 and operable to separate the separate the gaseous stream 12, the adducts 16, and the saturated $C_{5+}$ hydrocarbon stream 14. The separator 106 may operate at a relatively lower pressure than the hydrodesulfurization unit 104. The separator 106 may operate at a pressure of from approximately 0.01 MPa (vacuum pressure) to 0.5 MPa. In other words, the separator may have an operating pressure of approximately atmospheric pressure.

In some embodiments, a venting port may be interposed between the hydrodesulfurization reactor 104 and the separator 106 and fluidly connected to both. The venting port may be operable to vent the gaseous stream 12, including hydrogen sulfide gas, off from the adducts 16 and the saturated $C_{5+}$ hydrocarbon stream 14 coming from the hydrodesulfurization unit, thereby separating the gaseous stream 12 and forming a desulfurized liquid stream. Thereby, the separator 106 may be operable to separate the saturated $C_{5+}$ hydrocarbon stream 14 and the adducts 16 from each other. The venting port may also be operable to reduce the pressure of the liquid stream prior to the liquid stream's entry into the separator 106.

The separator 106 (as the first distillation tower) may separate the adducts 16 from the gaseous stream 12, the saturated $C_{5+}$ hydrocarbon stream 14, or both at a cut point of approximately 80° C., or from 50° C. to 250° C., from 50° C. to 70° C., from 70° C. to 80° C., from 80° C. to 90° C., from 90° C. to 150° C., from 150° C. to 200° C., from 200° C. to 250° C., or any combination of ranges or smaller range therein, such as from 75° C. to 85° C. In this manner, the adducts 16 may be a 'bottoms' fraction that may exit through the bottom of the first distillation tower 106 at any one of the previous cut points or cut point ranges.

Still referring to FIG. 1, the first thermal cracking reactor 108 may be fluidly connected to, and downstream of, the separator 106. The first thermal cracking reactor 108 may crack the adducts 16 to produce at least a decomposed adduct stream 18. The decomposed adduct stream 18 may include alpha olefin stream 20 and recovered conjugated diene compound stream 22. The decomposed adduct stream may also be referred to as a "cracked adduct stream" 18, according to embodiments herein. The alpha olefin stream 20 may also be regarded as a "desulfurized alpha olefin stream" 20, according to embodiments herein.

The alpha olefin stream 20 may also include branched alpha olefins and internal olefins recovered from the branched alpha olefin adducts and the internal olefin adducts, respectively. However, as previously discussed, the steric hindrance from the previous may make the branched alpha olefins and internal olefins less present in the alpha olefin stream 20 than the linear alpha olefins. In other words, the alpha olefin stream 20 may include a greater amount of linear alpha olefins than either branched alpha olefins or internal olefins.

In the embodiments herein, various reactors are considered suitable for the first thermal cracking reactor 108. For example, and in embodiments first thermal cracking reactor 108 may be a tubular-type reactor, vessel-type reactor, batch-type reactor such as autoclave reactor, or continuous stirred-tank reactor (CSTR). In other words, the first thermal cracking reactor 108 may be configured to form the decomposed adduct stream 18 in batch mixing or continuous mixing. Without being limited by theory, a catalyst may not be preferred for use with the first thermal cracking reactor, as basic or acidic catalysts may tend to isomerize alpha olefins, rendering pointless the adduct formation steps. In other words, the first thermal cracking reactor may not include a catalyst.

The first thermal cracking reactor 108 may operate at a temperature of greater than 200° C., such as from 200° C. to 250° C., from 250° C. to 275° C., from 275° C. to 300° C., from 300° C. to 350° C., from 350° C. to 375° C., from 375° C. to 400° C., or any combination of ranges or smaller range therein, such as from 200° C. to 400° C. Without being limited by theory, the first thermal cracking reactor 108 operating at a temperature of greater than 200° C. may operate to crack the adduct pair into the alpha olefins 20 and recovered conjugated diene compound 22 in an endothermic decomposition reaction that is the reverse of the Diels-Alder reaction in the Diels-Alder reactor 102, an example of which is shown by the reverse of Equation 1 above.

The first thermal cracking reactor 108 may also be additionally configured to receive an injected inert gas, including but not limited to nitrogen, helium, argon, or combinations thereof.

The first thermal cracking reactor 108 may operate at a pressure of from 0.45 MPa to 6.31 MPa. The first thermal cracking reactor may also be operated at a pressure of from 0.45 MPa to 0.79 MPa, from 0.79 MPa to 1.48 MPa, from 1.48 MPa to 2.86 MPa, from 2.86 MPa to 4.24 MPa, from 4.24 MPa to 5.62 MPa, from 5.62 MPa to 6.31 MPa, or any combination of ranges or smaller range therein.

The first thermal cracking reactor 108 may operate with a residence time of between 6 minutes to 180 minutes. The hydrodesulfurization reactor 104 may operate with a residence time of from 6 minutes to 12 minutes, from 12 minutes to 30 minutes, from 30 minutes to 60 minutes, from 60 minutes to 120 minutes, from 120 minutes to 180 minutes, or any combination of ranges or smaller range therein, such as from 12 minutes to 60 minutes.

As previously stated, "desulfurized" may refer to a substance having a sulfur content of less than 20 parts per million. For example, and in embodiments, the adducts 16 and/or the decomposed adduct stream 18 may be desulfurized and have a sulfur content of less than 20 parts per millions, such as from 1 ppm to 19 ppm, from 1 ppm to 5 ppm, from 5 ppm to 10 ppm, from 10 ppm to 15 ppm, from 15 ppm to 18 ppm, from 18 ppm to 19 ppm, or any combination of ranges or smaller range therein, such as from 15 to 19 ppm. In other words, the adducts 16 and/or the decomposed adduct stream 18 may, in at least some embodiments, be considered 'sweet.'

Still referring to FIG. 1, and as previously stated, the systems 100 and 200 may include the second distillation tower 110, which may also be regarded as a second separator. The second distillation tower 110 may be fluidly connected to, and downstream of, the thermal cracking reactor 108. The second distillation tower 110 may separate the alpha olefins 20 and/or the recovered conjugated diene compound 22 from the decomposed adduct stream 18. The second distillation tower 110 may separate the alpha olefins 20 and/or the recovered conjugated diene compound 22 from the cracked adduct stream 12 at a cut point of approximately 322° C., or from 300° C. to 400° C., from 300° C. to 310° C., from 310° C. to 330° C., from 330° C. to 350° C., from 350° C. to 380° C., from 380° C. to 400° C., or any combination of ranges, or smaller range, therein, such as from 320° C. to 330° C.

The second distillation tower 110 may also be fluidly connected to the Diels-Alder reactor 102. The second distillation tower may send the recovered conjugated diene compound to the Diels-Alder reactor 102 to be re-used as the conjugated diene compound 4. Without being limited by theory, it is also contemplated that the recovered conjugated diene compound may undergo one or more additional treatments before entering the Diels-Alder reactor 102 to render the recovered conjugated diene compound suitable for re-use. Make-up conjugated diene compound from an external source may also be used to supplement the recovered conjugated diene compound and to make up for conjugated diene compound 4 consumed in the processes herein. A portion of alpha olefin stream 20 may also be passed to the Diels-Alder reactor 102 with the recovered conjugated diene compound. For the reasons previously elaborated on, the recycling of the alpha olefin stream 20 may allow for further purification of alpha olefins over internal olefins (non-alpha olefins). Likewise, the recycling of the alpha olefin stream 20 may allow for further purification of linear alpha olefins over branched alpha olefins.

Now referring to FIG. 2, a system 200 may be similar or identical in some respects to that of FIG. 1 and system 100. The system 200 may further include a crude oil refining process 112 fluidly connected to, and upstream of, the Diels-Alder reactor 102. The crude oil refining process 112 may include one or more of a supercritical water reactor, pyrolysis unit, hydrocracker, hydrotreater, non-catalytic steam cracker, steam catalytic cracker, or fluid catalytic cracker. The crude oil refining process 112 may upgrade a crude oil 24 (feed stream) to form an upgraded crude oil. The crude oil refining process 112 may further include an initial separation unit downstream of the previous units and configured to separate the upgraded crude oil to form a heavy upgraded crude oil and a light upgraded crude oil. The light upgraded crude oil may be the hydrocarbon oil stream.

As previously mentioned, the crude oil refining process may include a supercritical water reactor. The supercritical water reactor may be fluidly connected to, and upstream of, the Diels-Alder reactor 102. The supercritical water reactor may crack the crude oil 24 in the presence of supercritical water 26 to form the upgraded crude oil, which may also be the hydrocarbon oil stream 2. The crude oil 24, may include a paraffin feedstock or any of the crude oils previously mentioned.

The supercritical water reactor may operate at a temperature of less than 500° C., such as from 373° C. to 390° C., from 390° C. to 410° C., from 410° C. to 430° C., from 430° C. to 440° C., or from 440° C. to 449° C., from 449° C. to 500° C., or any combination of ranges or smaller range therein, such as from 373° C. to 500° C. The supercritical water reactor may also operate at a temperature of from approximately 22 MPa to 41.47 MPa, such as from approximately 22 MPa to 33.2 MPa, from 33.2 MPa to 37.33 MPa, from 37.33 MPa to 41.47 MPa, or any combination of ranges or smaller range therein. Without being limited by theory, the supercritical water reactor may operate at any temperature and pressure operable to maintain water in a supercritical condition, such as those listed above.

The supercritical water reactor may have a residence time of from 0.1 minutes to 60 minutes, such as from 0.1 minutes to 0.2 minutes, from 0.2 minutes to 1 minute, from 1 minute to 5 minutes, from 5 minutes to 10 minutes, from 10 minutes to 30 minutes, from 30 minutes to 60 minutes, or any combination of ranges or smaller range therein. Without being limited by theory residence time may be estimated by assuming internal fluid in the supercritical water reactor is 100% water.

Without being limited by theory, the cracking of the feed stream 24 in the presence of the supercritical water 26 may operate to convert sulfur compounds that may be present in the feed stream 24, such as sulfides, disulfides, and thiols, into olefins, hydrogen sulfide, mercaptans, and elemental sulfur. Accordingly, the conversion of the sulfides, disulfides, thiols in the supercritical water reactor before the Diels-Alder reactor 102 may remove sulfur compounds from the hydrocarbon oil stream 2 before the Diels-Alder reactions. The removal of these sulfur compounds may thereby increase the degree of desulfurization of the hydrocarbon oil stream 2 in the systems and process discussed herein. Without being limited by theory, the removal of these sulfur compounds may also reduce the need severity of the hydrodesulfurization reactions, which may also reduce the degree of saturation of the non-adduct olefins. However, other sulfur compounds, such as thiophenes, benzothiophenes, or dibenzothiophenes, may be stable in the first thermal cracking reactor and at temperatures of less than 500° C. As previously discussed however, thiophenes, benzothiophenes, and dibenzothiophenes are also inert in the Diels-Alder reactor and may be removed in the hydrodesulfurization reactor 104. Thereby, the system 200 may allow the conversion of a cheap unrefined feedstock in the form of a crude oil into valuable intermediates such as alpha olefins with trace sulfur content.

Referring back to FIG. 1, embodiments of the present disclosure also include processes for producing the alpha olefins 20. The processes may include any of the systems 100, 200 previously described.

The process may include reacting the conjugated diene compound 4 and a hydrocarbon oil stream 2 that includes alpha olefins in a Diels-Alder reactor 102 at a temperature of 100° C. to 250° C. to form the effluent stream 6. The process may further include subjecting the effluent stream 6 from the Diels-Alder reactor 102 to the hydrodesulfurization catalyst and the hydrogen stream 8 in the hydrodesulfurization reactor 104 to produce the hydrodesulfurized effluent stream 10. As previously stated, the hydrodesulfurized effluent stream 10 may include the adducts 16 of the conjugated diene compound 4 and the alpha olefins, the saturated $C_{5+}$ hydrocarbon stream 14, and the gaseous stream 12.

The process may then further include separating the adducts 16, the saturated $C_{5+}$ hydrocarbon stream 14, and the gaseous stream 12. Separating the adducts 16, the saturated $C_{5+}$ hydrocarbon stream 14, and the gaseous stream 12 may further include venting the gaseous stream 12 from the adducts 16 and the saturated $C_{5+}$ hydrocarbon stream 14; as well as separating the adducts 16 from the saturated $C_{5+}$ hydrocarbon stream 14 in the first distillation tower 106. Separating the adducts 16, the saturated $C_{5+}$ hydrocarbon stream 14, and the gaseous stream 12 may also include separating the adducts 16 from the gaseous stream 12 and the saturated $C_{5+}$ hydrocarbon stream 14 in a first distillation tower 106.

The process may also include cracking the adducts 16 in the first thermal cracking reactor 108 to produce the decomposed adduct stream 18, the decomposed adduct stream 18 including the alpha olefin stream 20 and the recovered conjugated diene compound stream 22. As previously stated, the first thermal cracking reactor 108 may operate at a temperature of greater than 250° C., which may be sufficient to decompose the adducts 16 into alpha olefins and recovered conjugated diene compound.

The process may further include separating the alpha olefin stream 20 and the recovered conjugated diene compound stream 22 in the second distillation tower 110. Further, the recovered conjugated diene compound stream 22 may be passed to the Diels-Alder reactor 102 to be re-used/recycled as the conjugated diene compound 4. The alpha olefin stream 20 may also be passed to the Diels-Alder reactor 102 as additional alpha olefins in the hydrocarbon oil stream 2. Without being limited by theory, another iteration of upgrading of the alpha olefin stream 20 in the processes herein may further preferably generate linear alpha olefins rather than branched alpha olefins and internal olefins, for the reasons stated hereinabove.

Now referring back to FIG. 2, the process may also include introducing the crude oil (feed stream) 24 to the crude oil refining process 112. As previously discussed, this may include one or more of supercritical water upgrading, pyrolysis, hydrocracking, hydrotreating, non-catalytic steam cracking, steam catalytic cracking, or fluid catalytic cracking to form the upgraded crude oil. The upgraded crude oil may then be separated at a cut point of from 340° C. to 400° C., including approximately 340° C. or approximately 400° C., to form the heavy upgraded crude oil and the light upgraded crude oil. The light upgraded crude oil may include one or more of paraffins, linear alpha olefins, branched alpha olefins, internal olefins, aromatics, sulfur compounds, and nitrogen compounds. The light upgraded crude oil may include at least 5 wt. % linear alpha olefins by weight of the light upgraded crude oil, such as from 5 wt. % to 7.5 wt. %, from 7.5 wt. % to 10 wt. %, from 10 wt. % to 12.5 wt. %, from 12.5 wt. % to 20 wt. %, or from 20 wt. % to 99 wt. % linear alpha olefins. In other words, the hydrocarbon oil stream 2 may include a feed stream previously upgraded by traditional upgrading processes.

Still referring to FIG. 2, the process may include introducing the crude oil 24 to the supercritical water reactor in the presence of the supercritical water 26, to thereby form the hydrocarbon oil stream 2.

EXAMPLES

The various embodiments of processes and systems for the production of desulfurized alpha olefins will be further clarified by the following examples. The examples are illustrative in nature, and should not be understood to limit the subject matter of the present disclosure.

Example 1

A crude oil feedstock was processed in a laboratory experiment modeling the systems illustrated in FIGS. 1 and 2. The compositions of the feedstock used in the Examples are shown below in Table 1. Further, Tables 1 and 2 illustrates the composition of the feedstock after upgrading in a thermal cracking reactor in the presence of supercritical water, as discussed in embodiments hereinbefore. This upgraded feedstock was then used as the hydrocarbon oil stream for the experiments. Hydrocarbon oil was obtained from distillation of the thermal cracking reactor effluent with cut point of 313° C. for $T_{95}$ As used herein, "$T_N$ boiling point" refers to the temperature at which greater than "N wt. %" of components in a hydrocarbon composition are boiling. For example, and as shown below in Table 1, the feedstock having a $T_5$ boiling point of 376° C. means that 5 wt. % of the feedstock is still boiling at 376° C.

TABLE 1

Feedstock and Hydrocarbon Oil Composition

| Feed Quality | Feedstock | Hydrocarbon Oil |
| --- | --- | --- |
| Degrees API | 12.8 | 42.1 |
| Sulfur Content, wt. % | 3.9 | 0.52 |
| Sulfur Content, parts per million | 39,000 | 5200 |
| Viscosity at 49° C., centistokes | 615 | — |
| Distillation | ASTM D 7169 | ASTM D 2287 |

| $T_N$ Boiling Point | Temperature (° C.) | |
| --- | --- | --- |
| 5% | 376 | 81 |
| 10% | 400 | 99 |
| 30% | 462 | 125 |
| 50% | 521 | 216 |
| 70% | 585 | 229 |
| 90% | 670 | 299 |
| 95% | 702 | 313 |

TABLE 2

Hydrocarbon Oil Composition

| Fraction | Weight Percent (%) |
| --- | --- |
| Paraffins | 33.8 |
| Alpha Olefins | 18.9 |
| Non-Alpha Olefins | 8.9 |
| Iso-Paraffins | 12.7 |
| Naphthene | 8.5 |
| Aromatics | 14.6 |
| Other | 2.6 |

Diels-Alder Reactor

Two hundred grams of the hydrocarbon oil of Tables 1 and 2 was then placed in an Autoclave-type reactor with 48.1 grams of reagent grade anthracene, provided by Sigma Aldrich) to model the Diels-Alder reactor 102. The alpha olefins in the hydrocarbon oil had an average molecular weight of 154.3 grams per mole and anthracene has a molecular weight of 178.23 grams per mole. Accordingly, a ratio of approximately 0.91:1 alpha olefins to anthracene was used.

After introducing the hydrocarbon oil and the anthracene, the reactor was purged with nitrogen gas for thirty minutes while rotating an agitator at 200 rotations per minute (RPM) within the reactor to remove air. After the nitrogen purging, the reactor was charged with nitrogen at approximately 2.17 MPa. Temperature of the reactor was increase to 230° C. at a ramp of 5° C. per minute, then maintained at that temperature for three hours at the same 200 RPM agitation. After the three hours, the reactor was cooled to approximately 50° C. through a cooling coil inside the reactor.

Hydrodesulfurization Reactor

The effluent from the reactor was then sent to another similar Autoclave-type reactor, this reactor modeling the hydrodesulfurization reactor 104 with a pre-sulfided hydrodesulfurization catalyst of molybdenum and cobalt on an activated carbon support prepared in the below manner.

A 20.0 g sample of dried and purified activated carbon (Norit) having specific surface area of 1,065 m$^2$/g and average pore diameter of 2.2 nm was placed in a 200 mL flask. The flask was then evacuated under vacuum for approximately 16 hours to a pressure of approximately 1 torr. An aqueous solution was prepared by dissolving 4.91 g (0.00397 mol) of $(NH_4)_6Mo_7O_{24} \cdot 4H_2O$ (Fluka) to make 20 mL (0.20 M) aqueous solution. The aqueous solution (20 mL) was added dropwise and shaken over a period of about 5 minutes into the flask, which was maintained under vacuum, and mixed for approximately 6 hours. Following mixing, the flask was vented to the atmosphere and heated at a temperature of approximately 120° C. until the atmospheric vaporization of water ceased. The flask was cooled to room temperature and evacuated under vacuum to a pressure of approximately 1 torr for approximately 16 hours.

Following this, a 8.02 g (0.00649 mol) sample of $(NH_4)_6Mo_7O_{24} \cdot 4H_2O$ (Fluka) was dissolved in water to make 40 mL (0.16M) aqueous solution. A 20 mL sample of the aqueous solution was then introduced to the above flask dropwise over about a 5 minute period with shaking, under vacuum, and mixed for approximately 6 hours. The flask was then vented to atmosphere and to a temperature of approximately 70° C. until the atmospheric vaporization of water ceased. The flask was cooled to room temperature and evacuated under vacuum to a pressure of approximately 1 torr for approximately 16 hours again.

Further, a 7.06 g (0.0243 mol) sample of $Co(NO_3)_2 \cdot 6H_2O$ (Aldrich Chem.) was dissolved in water to make a 20 mL aqueous solution (1.2M). The aqueous solution (20 mL) was introduced to the above flask dropwise over about a 5 minute period with shaking, under vacuum, and mixed for approximately 6 hours. After mixing, the flask was then vented to atmosphere and heated to a temperature of approximately 70° C. until the atmospheric vaporization of water ceased. The contents of the flask, a black powder, was transferred to an alumina crucible, heated at a rate of approximately 2° C. per min to a temperature of 320° C. and calcinated for approximately three hours under flowing nitrogen gas of atmospheric pressure.

The catalyst product (29 g) was collected as a black particulate material, consisting of approximately 25 wt. % molybdenum oxide and 6.2 wt. % cobalt oxide, which was further crushed and presulfided by a stream of 95 vol. % hydrogen and 5 vol. % hydrogen sulfide at 340° C. for three hours to obtain the final hydrodesulfurization catalyst.

After adding the effluent stream and the catalyst to the hydrodesulfurization reactor, the reactor was purged sequentially with nitrogen to remove air and hydrogen to remove the nitrogen. The reactor was then charged with hydrogen at approximately 2.58 MPa to model the hydrodesulfurization reactor 104. The reactor was then heated to 240° C. at a rate of 5° C. per minute, then maintained at that temperature for sixty minutes while rotating an agitator of the reactor at 200 RPM. After the sixty minutes, the reactor was vented to atmospheric pressure and purged with nitrogen to remove sulfur and hydrogen sulfide before exposing the reactor effluent to air.

First Distillation Tower

Two hundred and forty (240) grams of the reactor effluent was then recovered from the hydrodesulfurization reactor and subjected to a batch-type distillation unit under vacuum pressure (50 Torr) to model the first distillation tower 106 and separate the distillate from the other effluent. The cut point of the distillation was approximately 80° C. and approximately 235 grams of a distillate were recovered.

First Thermal Cracker

The 235 grams of the distillate were then introduced to another similar Autoclave-type reactor to model the first thermal cracker 108. The reactor was purged with nitrogen for thirty minutes while stirring with an agitator at 200 RPM. The reactor was then charged with nitrogen at approximately 2.51 MPa. The reactor was then heated to 320° C. at a rate of 5° C. per minute, then maintained at that temperature for thirty minutes while rotating the agitator of the reactor at 200 RPM. After the thirty minutes, the reactor was cooled to approximately 50° C. through a cooling coil inside the reactor.

Second Distillation Tower

Two hundred and twenty-nine (229) grams of the reactor effluent was then recovered from the first thermal cracker and subjected to a batch-type distillation unit under vacuum pressure (50 Torr) to model the second distillation tower 110 and separate a distillate containing the desulfurized alpha olefins from the other effluent. The cut point of the distillation was approximately 322° C. and approximately 42 grams of the residue was recovered. The composition of the distillate is shown below in Table 3.

For comparison, the same hydrocarbon oil of Tables 2 and 3 was also exposed to the process of Example 1 without the Diels-Alder reactor. The composition of the distillate of the comparative example is also shown below in Table 3.

TABLE 3

Distillate (Product) Composition

| Example 1 | | Comparative Example (without Diels-Alder) | |
|---|---|---|---|
| Fraction | Weight Percent (%) | Fraction | Weight Percent (%) |
| Paraffins | 50.9 | Paraffins | 65.6 |
| Alpha Olefins | 16.8 | Alpha Olefins | 0.6 |
| Non-Alpha Olefins | 0.1 | Non-Alpha Olefins | 0.1 |
| Iso-Paraffins | 13.5 | Iso-Paraffins | 13.2 |
| Naphthene | 3.8 | Naphthene | 4.6 |
| Aromatics | 13.7 | Aromatics | 14.0 |
| Other | 1.2 | Other | 1.9 |
| Measurement | Parts Per Million | Measurement | Parts Per Million |
| Sulfur Content | 18 | Sulfur Content | 450 |

As shown above in Table 3. Example 1 resulted in a distillate with a large percentage of alpha olefins and almost no non-alpha olefins. In contrast, the Comparative Example included almost no olefins (0.7 wt. % total) of any type. Further, Example 1 showed a significant reduction in sulfur content of from 39,000 ppm to 18 ppm for an untreated crude oil, and from 5,200 ppm to 18 ppm for a pre-treated crude oil. In contrast, the Comparative Example still showed significantly greater sulfur content when the Diels-Alder reactor was not utilized. Without being limited by theory, the decreased effectiveness of the hydrodesulfurization in the Comparative Example may be attributable to the presence of non-adduct olefins inhibiting the hydrodesulfurization reaction, thereby saturating the olefins and resulting in both less olefin yield and greater sulfur content.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

It is also noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

What is claimed is:

1. A process for producing desulfurized alpha olefins, the process comprising:
    reacting a conjugated diene compound and a hydrocarbon oil stream comprising alpha olefins in a Diels-Alder reactor at a temperature of 100° C. to 250° C. to form an effluent stream comprising adducts of the conjugated diene compound and the alpha olefins;
    subjecting the effluent stream to a hydrodesulfurization catalyst and a hydrogen stream in a hydrodesulfurization reactor to produce a hydrodesulfurized effluent stream comprising the adducts of the conjugated diene compound and the alpha olefins, a saturated $C_{5+}$ hydrocarbon stream, and a gaseous stream, wherein the gaseous stream comprises hydrogen, sulfides, $C_1$-$C_4$ saturated hydrocarbons, or combinations thereof;
    separating the adducts of the conjugated diene compound and the alpha olefins, the saturated $C_{5+}$ hydrocarbon stream, and the gaseous stream; and
    cracking the adducts of the conjugated diene compound and the alpha olefins in a first thermal cracking reactor operating at a temperature greater than 250° C. to produce a decomposed adducts stream comprising an alpha olefin stream and a recovered conjugated diene compound stream.

2. The process of claim 1, wherein a molar ratio of the conjugated diene compound to alpha olefins entering the Dies-Alder reactor is from 0.1:1 to 5:1 conjugated diene compound to alpha olefins.

3. The process of claim 1, wherein the conjugated diene compound comprises substituted anthracene, unsubstituted anthracene, cyclohexadiene, cyclopentadiene, or combinations thereof.

4. The process of claim 1, wherein:
    the hydrocarbon oil stream has a sulfur content of from 20 ppm to 50,000 ppm; and
    the alpha olefin stream has a sulfur content of less than 20 ppm.

5. The process of claim 1, wherein the hydrocarbon oil stream comprises a crude oil with an API gravity of from 25° to 50°.

6. The process of claim 1, wherein separating the adducts of the conjugated diene compound and the alpha olefins, the saturated $C_{5+}$ hydrocarbon stream, and the gaseous stream further comprises:
    venting the gaseous stream from the adducts of the conjugated diene compound and the alpha olefins and the saturated $C_{5+}$ hydrocarbon stream; and
    separating the adducts of the conjugated diene compound and the alpha olefins from the saturated $C_{5+}$ hydrocarbon stream in a first distillation tower operating at a cut point of from 50° C. to 250° C.

7. The process of claim 1, wherein separating the adducts of the conjugated diene compound and the alpha olefins, the saturated $C_{5+}$ hydrocarbon stream, and the gaseous stream further comprises;
    separating the adducts of the conjugated diene compound and the alpha olefins from the gaseous stream and the saturated $C_{5+}$ hydrocarbon stream in a first distillation tower operating at a cut point of from 50° C. to 250° C.

8. The process of claim 1, further comprising separating the alpha olefin stream from the recovered conjugated diene compound stream in a second distillation tower at a cut point of from 300° C. to 400° C.

9. The process of claim 1, wherein the hydrodesulfurization catalyst comprises:

a first metal selected from the group consisting of iron, ruthenium, osmium, cobalt, rhenium, iridium, nickel, palladium and platinum;

a second metal selected from the group consisting of iron, ruthenium, osmium, cobalt, rhenium, iridium, nickel, palladium and platinum; and a support selected from activated carbon, activated carbon fiber, carbon black, activated carbon fabric, activated carbon honeycomb, silicon dioxide, titanium dioxide, aluminum oxide, and zirconium dioxide.

10. The process of claim 9, wherein:

the hydrodesulfurization catalyst is selected from CoMo, NiMo, and NiCoMo; and the support is selected from aluminum oxide, silica oxide, and activated carbon.

11. The process of claim 10, wherein:

the molybdenum content is from 2 wt. % to 10 wt. % measured by weight of the hydrodesulfurization catalyst; and the cobalt content, the nickel content, or both, is from 0.2 wt. % to 25 wt. % measured by weight of the hydrodesulfurization catalyst.

12. The process of claim 1, further comprising passing the recovered conjugated diene compound stream to the Diels-Alder reactor to be re-used as the conjugated diene compound.

13. The process of claim 1, further comprising passing the alpha olefin stream from the first thermal cracking reactor to the Diels-Alder reactor as additional alpha olefins in the hydrocarbon oil stream.

14. The process of claim 1, further comprising introducing a crude oil to a supercritical water reactor in the presence of supercritical water, at a temperature of from 500° C. to 600° C., to form the hydrocarbon oil stream.

15. The process of claim 1, further comprising:

introducing a crude oil to a crude oil refining process comprising one or more of supercritical water upgrading, pyrolysis, hydrocracking, hydrotreating, non-catalytic steam cracking, steam catalytic cracking, or fluid catalytic cracking to form an upgraded crude oil; and separating the upgraded crude oil at a cut point of from 340° C. to 400° C. to form a heavy upgraded crude oil and the hydrocarbon oil stream, wherein:

the hydrocarbon oil stream comprises one or more of paraffins, linear alpha olefins, branched alpha olefins, internal olefins, aromatics, sulfur compounds, and nitrogen compounds, the hydrocarbon oil stream comprises at least 5 wt. % linear alpha olefins by weight of the hydrocarbon oil stream, the hydrocarbon oil stream comprises at least 100 ppm sulfur compounds, and the conjugated diene compound is selected from substituted and unsubstituted anthracene.

16. The process of claim 1, wherein the Diels-Alder reactor, the first thermal cracking reactor, the hydrodesulfurization reactor, or combinations thereof are a tubular-type reactor or continuous stirred-tank reactor.

17. A system for producing desulfurized alpha olefins, the system comprising:

a Diels-Alder reactor configured to form an effluent stream from a hydrocarbon oil stream and a conjugated diene compound, the effluent stream comprising adducts of the conjugated diene compound and alpha olefins from the hydrocarbon oil stream;

a hydrodesulfurization reactor comprising a hydrodesulfurization catalyst fluidly connected and downstream of the Diels Alder reactor;

a first distillation tower fluidly connected and downstream of the hydrodesulfurization reactor;

a first thermal cracking reactor fluidly connected and downstream of the first distillation tower; and a second distillation tower fluidly connected and downstream of the first thermal cracking reactor.

18. The system of claim 17, wherein:

the conjugated diene compound comprises substituted anthracene, unsubstituted anthracene, cyclohexadiene, cyclopentadiene, or combinations thereof;

the hydrodesulfurization catalyst is selected from CoMo, NiMo, and NiCoMo; and the support is selected from aluminum oxide, silica oxide, and activated carbon.

19. The system of claim 17, further comprising a supercritical water reactor fluidly connected and upstream of the Diels-Alder reactor, wherein the supercritical water reactor is configured to operate at a temperature of from 500° C. to 600° C.

20. The system of claim 17, wherein:

the system further comprises a venting port interposed between the hydrodesulfurization reactor and the first distillation tower, and fluidly connected to both;

the first distillation tower is configured to operate at a cut point of from 50° C. to 250° C.; and the second distillation tower is configured to operate at a cut point of from 300° C. to 400° C.

* * * * *

UNITED STATES PATENT AND TRADEMARK OFFICE
CERTIFICATE OF CORRECTION

PATENT NO. : 12,378,483 B2
APPLICATION NO. : 18/149458
DATED : August 5, 2025
INVENTOR(S) : Choi Page 1 of 1

It is certified that error appears in the above-identified patent and that said Letters Patent is hereby corrected as shown below:

In the Claims

Claim 8, Column 20, Line 63, delete "in a second distillation tower" and replace with -- in a distillation tower --.

Signed and Sealed this
Seventh Day of October, 2025

John A. Squires
*Director of the United States Patent and Trademark Office*